(12) United States Patent
Barber et al.

(10) Patent No.: US 7,513,862 B2
(45) Date of Patent: *Apr. 7, 2009

(54) SEED MAGAZINE

(75) Inventors: Jerry R. Barber, Ventura, CA (US); Charles R. Pitman, Santa Barbara, CA (US); Laust Pedersen, Santa Barbara, CA (US)

(73) Assignee: Core Oncology, Inc., Mercer Island, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/196,659

(22) Filed: Aug. 2, 2005

(65) Prior Publication Data

US 2005/0267320 A1   Dec. 1, 2005

Related U.S. Application Data (63) Continuation of application No. 10/354,950, filed on Jan. 29, 2003, now Pat. No. 6,953,426.

(51) Int. Cl.
*A61N 5/00* (2006.01)

(52) U.S. Cl. .......................................................... 600/7

(58) Field of Classification Search ................. 600/1–8; 604/37–48, 93.01, 57–64

See application file for complete search history.

(56) References Cited

U.S. PATENT DOCUMENTS

| | | |
|---|---|---|
| 2,620,796 A | 12/1952 | Eriksen et al. |
| 4,402,308 A | 9/1983 | Scott |
| 4,451,254 A | 5/1984 | Dinius et al. |
| 4,461,280 A | 7/1984 | Baumgartner |
| 4,692,628 A | 9/1987 | Sauerwein et al. |
| 4,700,692 A | 10/1987 | Baumgartner |
| 4,969,863 A | 11/1990 | van't Hooft et al. |
| 5,242,373 A | 9/1993 | Scott et al. |
| 5,342,283 A | 8/1994 | Good |
| 5,522,797 A | 6/1996 | Grimm |
| 5,561,698 A | 10/1996 | Mick et al. |
| 5,562,594 A | 10/1996 | Weeks |
| 5,860,909 A | 1/1999 | Mick et al. |
| 5,957,935 A | 9/1999 | Brown et al. |
| 6,102,844 A | 8/2000 | Ravins et al. |
| 6,213,932 B1 | 4/2001 | Schmidt |
| 6,256,529 B1 | 7/2001 | Holupka et al. |
| 6,267,717 B1 | 7/2001 | Stoll et al. |

(Continued)

FOREIGN PATENT DOCUMENTS

WO   WO 03/063944   8/2003

(Continued)

OTHER PUBLICATIONS

"Transperineal Ultrasound-Guided Prostate Seed Implant Accessories," The Complete Accessories Guide for the Seattle or Mick® Prostate Seed Delivery Systems! Mick Radio-Nuclear Instruments, Inc., 4 pgs.

(Continued)

*Primary Examiner*—John P Lacyk
(74) *Attorney, Agent, or Firm*—DLA Piper LLP (US)

(57) ABSTRACT

The invention provides magazines for radioactive brachytherapy seeds. The seed magazines provided herein include housing, seed holder, and pusher components, and optionally have a slidable shield to protect a user from radiation.

23 Claims, 11 Drawing Sheets

U.S. PATENT DOCUMENTS

| | | |
|---|---|---|
| 6,267,718 B1 | 7/2001 | Vitali et al. |
| 6,270,472 B1 | 8/2001 | Antaki et al. |
| 6,350,227 B1 | 2/2002 | Shikhman et al. |
| 6,358,195 B1 | 3/2002 | Green et al. |
| 6,361,487 B1 | 3/2002 | Green et al. |
| 6,366,633 B1 | 4/2002 | Stezaly et al. |
| 6,409,651 B1 | 6/2002 | Brown, III |
| 6,454,696 B1 | 9/2002 | Kindlein et al. |
| 6,572,527 B2 | 6/2003 | Steele, Sr. et al. |
| 6,953,426 B2 * | 10/2005 | Barber et al. ............ 600/7 |
| 2002/0013509 A1 | 1/2002 | Schmidt |
| 2002/0120174 A1 | 8/2002 | Steele, Sr. et al. |
| 2003/0144571 A1 | 7/2003 | Mick et al. |

OTHER PUBLICATIONS

"Product Update 98," Product Brochure, Mick Radio-Nuclear Instruments, Inc., 8 pgs.

"Mick® 200-TPV Applicator," Product Brochure, Mick Radio-Nuclear Instruments, Inc., 4 pgs.

"Mick® 200-TP Applicator Kit," Product Brochure, Mick Radio-Nuclear Instruments, Inc., 6 pgs.

"Prostate Brachytherapy," Mick News Flash 2000, 2000, vol. 1, Issue 1, Mick Radio-Nuclear Instruments, Inc., 6 pgs.

"Brachytherapy Seed Magazine Disposable, Spring-Loaded," Product Specification, Mick Radio-Nuclear Instruments, Inc., 2 pgs.

"Transperineal Ultrasound-Guided Prostate Seed Implants—The "Mick" System," Instrumentation and Accessories Guide, Mick Radio-Nuclear Instruments, Inc., 4 pgs.

"Transperineal Ultrasound-Guided Prostate Seed Implant Accessories," The Complete Accessories Guide for the Seattle or Mick® Prostate Seed Delivery Systems! Mick Radio-Nuclear Instruments, Inc., 18 pgs.

* cited by examiner

SEED MAGAZINE

CROSS-REFERENCE TO RELATED APPLICATIONS

This application is a continuation of U.S. application Ser. No. 10/354,950, filed Jan. 29, 2003, now U.S. Pat. No. 6,953,426.

TECHNICAL FIELD

This invention relates to magazines for radioactive seeds such as those used with brachytherapy devices.

BACKGROUND

Brachytherapy is a form of cancer treatment in which radiation sources are placed inside a patient's body to irradiate a tumor. In brachytherapy, a surgeon usually implants several radioactive seeds in or around a tumor, thus providing a radiation dose to the tumor. Careful placement of the radioactive seeds allows localized and precise irradiation of the tumor. Because the radiation dose diminishes rapidly outside the radioactive seed, the radiation dose to surrounding healthy tissues is minimized. Many forms of cancer respond to brachytherapy, including several forms of prostate cancer. Brachytherapy generally is less invasive than surgery, usually results in fewer side effects than surgery or external beam radiation, allows for a short recovery time, and reduces the impact on the patient's quality of life.

Radioactive seeds typically are rice grain sized (generally about 0.8 mm by 4.5 mm), roughly cylindrical objects containing very small amounts of radioactive material. In one widely practiced brachytherapy procedure, the radioactive seeds are implanted permanently inside the patient's body. The half-life of the radioactive material is generally short, and the radioactivity in the seeds decays after about three to six months to the point that there is little detectable radiation. Two radioactive isotopes commonly used for permanent implants are iodine-125, often used to treat slower growing tumors, and palladium-103, which is preferred when a tumor is fast growing. Other radioactive materials have been used in implants as well.

SUMMARY

The invention relates to magazines for holding radioactive objects such as brachytherapy seeds. In particular, the invention provides seed magazines having a housing, a seed holder, and a pusher. Seed magazines also can have a shield (e.g., a slidable shield) that can protect a user from radioactivity emitted by seeds contained within the magazines.

The seed magazines provided herein typically are configured for installation into a brachytherapy device (e.g., a brachytherapy seed applicator). During brachytherapy procedures, a seed applicator that is engaged with a seed magazine and attached to a needle is inserted into a patient for delivery of radioactive seeds to the patient. Blood cells can migrate from the patient into the seed applicator, and can become lodged in the applicator at or near magazine retaining structures designed to retain the seed magazine within the applicator. For example, blood and other debris can obstruct the proper functioning of the ball-plunger used to secure seed magazines into standard seed applicators such as the Mick® 200-TP and 200-TPV seed applicators.

The seed magazines provided herein can be configured to be installed in brachytherapy devices (e.g., Mick seed applicators) without engaging magazine retaining structures within the applicators. Such seed magazines therefore can be easily inserted into and removed from brachytherapy devices. In addition, the seed magazines provided herein can have springs or other structures to facilitate retention within brachytherapy devices, rather than relying on magazine retaining structures within such devices.

The seed magazines provided herein also can have markings to indicate how many seeds, if any, remain within the magazine. Thus, a user does not have to visualize the seeds to know how many seeds the magazine contains, reducing the user's exposure to radiation from the seeds.

The invention features a seed magazine having a housing, a seed holder, and a pusher, wherein the seed holder has a surface defining a recess at least one millimeter in length. The seed holder can have a proximal end and a distal end, and the recess can extend from the proximal end toward the distal end. The recess can define a channel that extends to an end of the seed holder. The recess can be centrally located between two edges of the surface. The recess can be defined by no more than two surfaces of the seed holder. The recess can be between three and eight millimeters in length (e.g., between five and six millimeters in length). The maximum width of the recess can be less than five millimeters (e.g., between 0.5 and 2.5 millimeters).

The seed holder can have two adjacent surfaces, where the first surface defines at least one spring and the second surface defines a space, and where the space is positioned such that the at least one spring can move at least partially into the space when force is applied to the first surface. The seed holder can have a surface, where the surface defines a protrusion, and where the protrusion exerts force against a brachytherapy device when the seed magazine is engaged with the brachytherapy device.

The seed magazine can further include a shield, where the seed holder defines a slot for retaining radioactive seeds, and where at least a portion of the shield is positioned over the seed holder. The shield can be slidably movable within the housing and the pusher. The shield can move slidably within the housing and the pusher to obstruct the view of radioactive seeds within the seed magazine.

The pusher can have markings. The space between the markings can be equal to the thickness of a seed.

The housing can be hollow. The external surface of the housing can define external threads and the internal surface of the housing can define internal threads, and the external and internal threads can have the same pitch. The external and internal threads can be offset to maximize the thickness of the housing between the external and internal threads.

The pusher can have a distal end and a disc at the distal end. The disc can define a circular shape with scalloped edges. The disc can be flexible. The thickness at the edge of the disc can be less than the thickness at a point away from the edge of the disc and closer to the center of the disc. The thickness from the edge to the center of the disc can be uniform. The disc can be concave or dome-shaped.

In another aspect, the invention features a seed magazine having a housing, a seed holder, a pusher, and a shield, where the seed holder defines a slot for retaining radioactive seeds, and where at least a portion of the shield is positioned over the seed holder. The shield can be slidably movable within the housing and the pusher. The shield can move slidably within the housing and the pusher to obstruct the view of radioactive seeds within the seed magazine.

In another aspect, the invention features a seed magazine having a housing, a seed holder, and a pusher, where the seed holder defines a slot for retaining radioactive seeds, where the seeds are not visible from outside the seed magazine, and where the pusher has markings to indicate the number of seeds within the seed magazine. The space between the markings can be equal to the thickness of a seed.

In yet another aspect, the invention features a seed magazine having a housing, a seed holder, and a pusher, where the seed holder defines a slot for retaining radioactive seeds, and where the slot has a depth between about 1.2 millimeters and 1.65 millimeters.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

The invention provides magazines for containing radioactive objects such as brachytherapy seeds. The seed magazines typically contain several components, including a housing, a seed holder, a pusher, and, optionally, a shield. These components can be made from any material. For example, the components can be made from a plastic material such as polysulfone, nylon, polypropylene, or polycarbonate, or from a metal such as stainless steel, titanium, or aluminum. Components also can be made from a plastic material that contains particles of a metal such as tungsten, titanium, lead, or stainless steel. The metal content can be from about 5 percent by weight to about 95 percent by weight (e.g., 6, 10, 15, 20, 25, 30, 35, 40, 45, 50, 55, 60, 65, 70, 75, 80, 85, 90, or 94 percent by weight). In some embodiments, the metal content of a seed magazine component can be about 40 percent to about 70 percent by weight (e.g., 41, 45, 50, 55, 60, 65, or 69 percent by weight). Seed magazine components made from such plastic and metal combinations can have plastic-like characteristics (e.g., flexibility) while providing radiation shielding.

Figure 1:
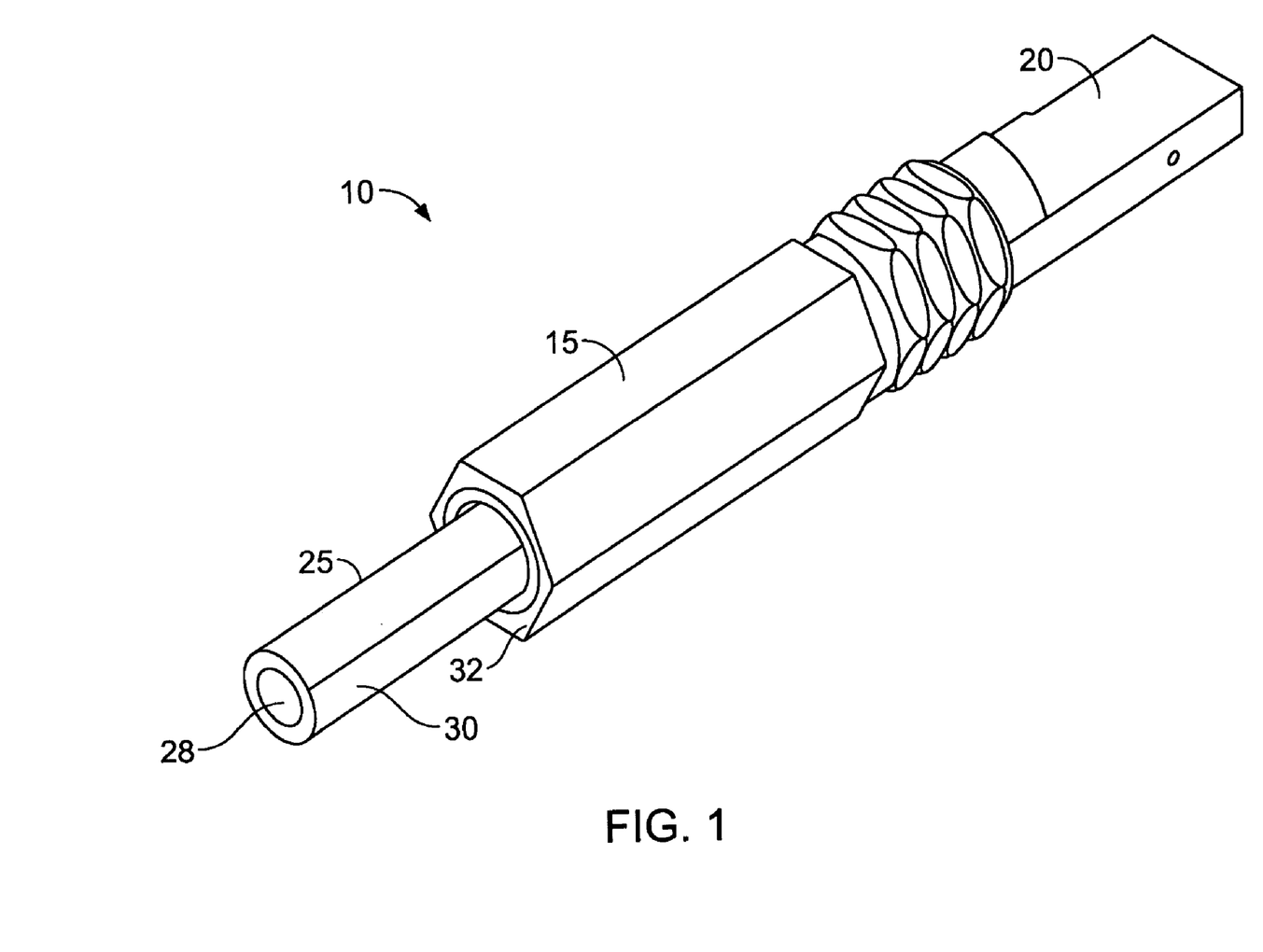
FIG. 1 is a side view of a seed magazine containing seeds.
Figure 2:
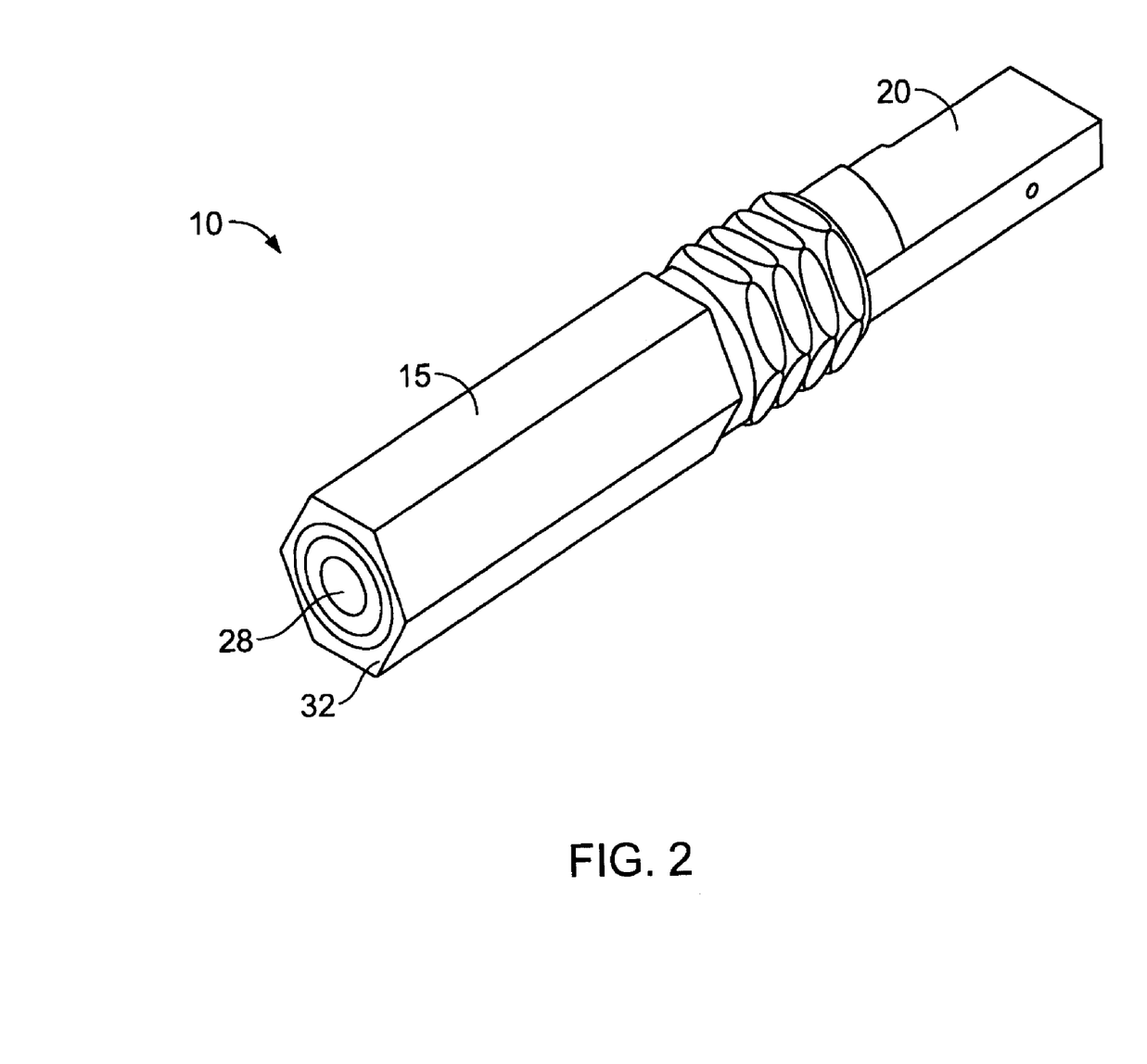
FIG. 2 is a side view of a seed magazine containing no seeds.

With reference to FIGS. 1 and 2, seed magazine 10 can have housing 15, seed holder 20, and pusher 25. Pusher 25 can have distal end 28 and gauge member 30. When seed magazine 10 contains seeds, distal end 28 and gauge member 30 of pusher 25 can protrude through distal end 32 of housing 15, as shown in FIG. 1. When seed magazine 10 contains no seeds, distal end 28 of pusher 25 can protrude through distal end 32 of housing 15, as shown in FIG. 2. In this embodiment, gauge 30 does not protrude through distal end 32 of housing 15 when seed magazine 10 contains no seeds. In some embodiments, however, gauge 30 can protrude through distal end 32 when seed magazine 10 contains no seeds.

Figure 3:
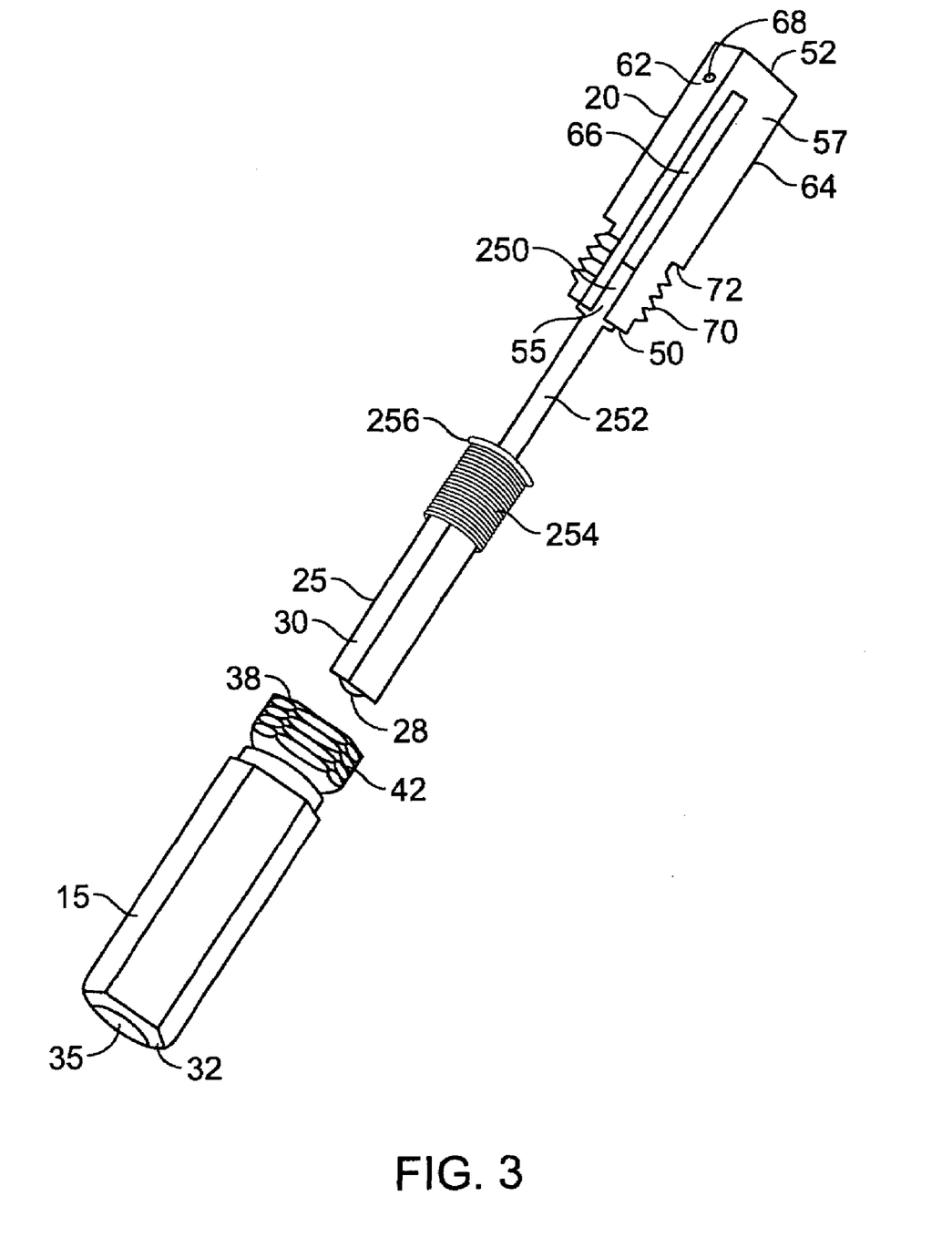
FIG. 3 is a side view of the components-of a disassembled seed magazine.
Figure 4:
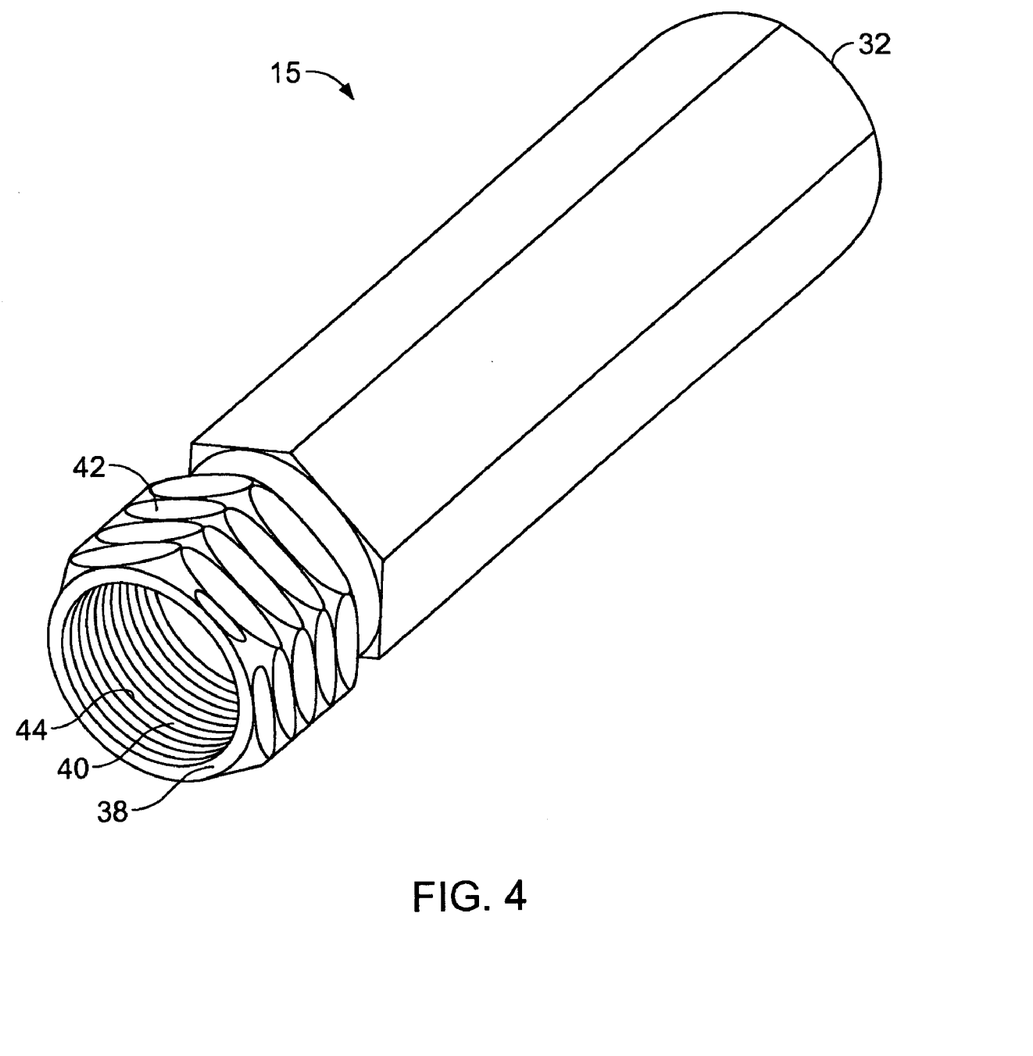
FIG. 4 is a side view of the housing of a seed magazine.

FIG. 3 depicts seed magazine 10 in disassembled form, showing housing 15, seed holder 20, and pusher 25 separate from one another. FIG. 4 shows a larger view of housing 15. A cross section of housing 15 can define any shape. As shown in FIG. 4, for example, a cross section of housing 15 can define a hexagonal shape. Alternatively, a cross section of housing 15 can define a circular, square, rectangular, or oval shape. With reference to FIGS. 3 and 4, housing 15 can be hollow, and distal end 32 of housing 15 can define distal opening 35 through which gauge 30 and/or distal end 28 of pusher 25 can protrude (e.g., when seeds are present in seed magazine 10). Housing 15 also can have proximal end 38, which can define proximal opening 40 of housing 15. The exterior surface of housing 15 near proximal end 38 can define external threads 42, which can be used to install seed magazine 10 in a brachytherapy device. For example, external threads 42 can be used to screw seed magazine 10 into a brachytherapy device such as a sterilization carrier or a seed loading device (e.g., a Mick® seed sterilizer insert or a Mick® seed loading V-block) that can be used to implant seeds into a patient. The interior surface of housing 15 can define internal threads 44. External threads 42 and internal threads 44 can have any pitch relative to one another. In some embodiments, external threads 42 and internal threads 44 have the same pitch, and can be offset relative to one another such that the thickness of the threaded portion of housing 15 is maximized. Such a configuration can allow for maximal strength of the threaded portion of housing 15.

Figure 5:
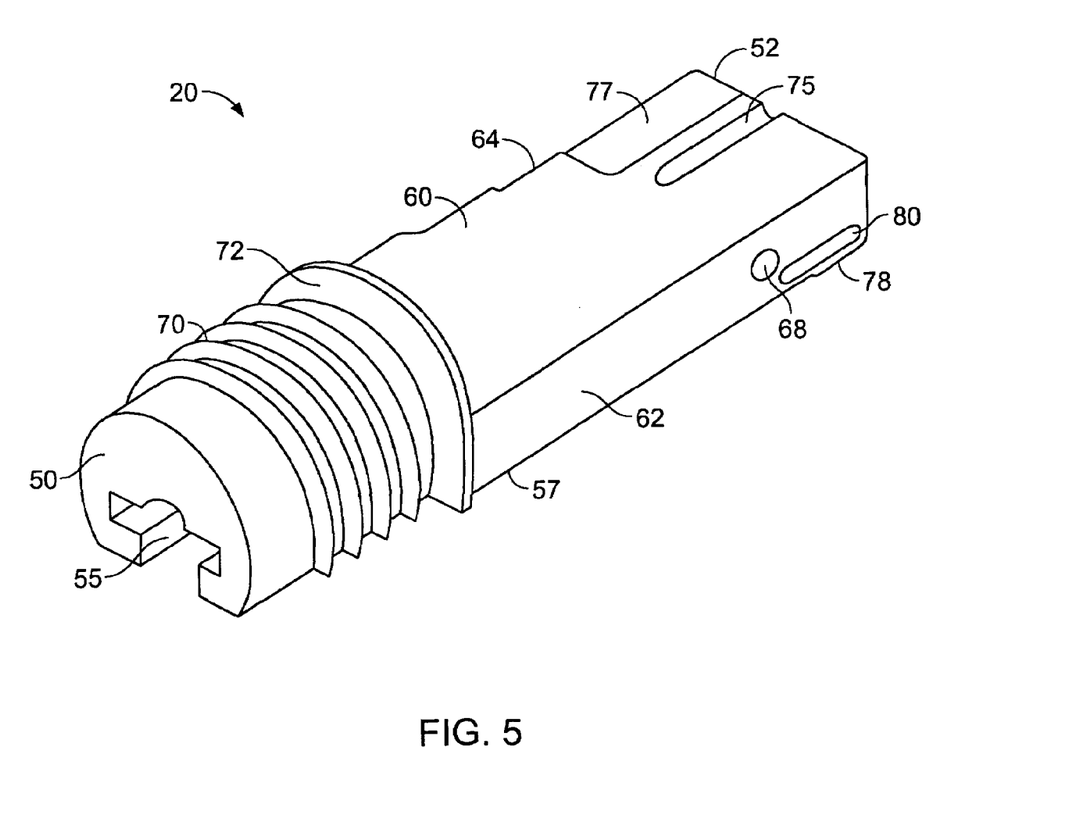
FIG. 5 is a side view of the seed holder of a seed magazine.

FIG. 5 is a side view of seed holder 20. With reference to FIGS. 3 and 5, seed holder 20 can have distal end 50 and proximal end 52. Seed holder 20 also can define slot 55, which can extend from distal end 50 toward proximal end 52, and which can be used to hold radioactive brachytherapy seeds, for example. Seed holder 20 can have top surface 57, bottom surface 60, first side surface 62, and second side surface 64. Top surface 57 can define opening 66 so that slot 55 and any seeds contained therein are visible. Alternatively, seed holder 20 may lack openings such that slot 55 is not visible through seed holder 20.

Figure 6:
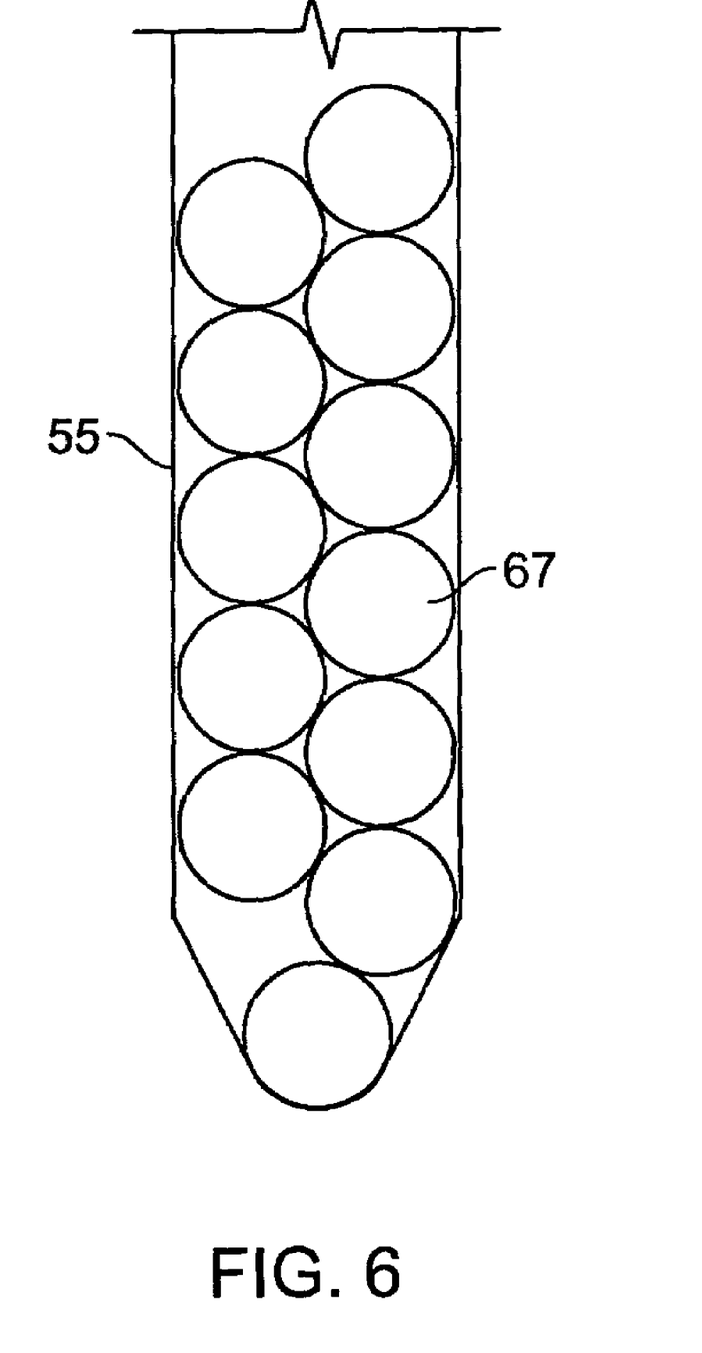
FIG. 6 is a cross-sectional view of two parallel rows of seeds in the slot of a seed holder.

Slot 55 can have any suitable size and can be configured to contain any number of brachytherapy seeds. Typically, slot 55 is slightly wider than the length of a brachytherapy seed, is slightly deeper than the diameter of a seed, and is long enough to hold the desired number of seeds. For example, slot 55 can be about three to about six millimeters wide (e.g., about 3, about 3.5, about 4, about 4.5, about 5, about 5.5, or about 6 millimeters wide), about 0.1 to about two millimeters deep (e.g., about 0.1, about 0.3, about 0.5, about 0.75, about 0.9, about 1, about 1.25, about 1.5, about 1.75, or about 2 millimeters deep), and can hold between 10 and 30 seeds (e.g., 10, 11, 12, 13, 14, 15, 16, 17, 18, 19, 20, 21, 22, 23, 24, 25, 26, 27, 28, 29, or 30 seeds). In another embodiment, slot 55 can have a depth that is about twice the diameter of a brachytherapy seed. For example, slot 55 can be between about 1.12 millimeters and about two millimeters deep (e.g., about 1.15, 1.2, 1.25, 1.3, 1.35, 1.4, 1.45, 1.5, 1.55, 1.6, 1.65, 1.7, 1.75, 1.8, 1.85, 1.9, 1.95, or about two millimeters deep). In such an embodiment, slot 55 can contain two parallel rows of brachytherapy seeds, and thus can hold between 20 and 60 seeds (e.g., 20, 22, 24, 25, 30, 35, 40, 45, 50, 55, 57, or 60 seeds). As shown in FIG. 6, the rows of seeds 67 can be staggered in slot 55.

With further reference to FIG. 5, seed holder 20 also can define channel 68, which can extend between first and second side surfaces 62 and 64 and through slot 55, and which can be positioned near proximal end 52 as shown in FIG. 3. When seed magazine 10 is installed in a brachytherapy device such as an applicator having a stylet, the stylet can be inserted through channel 68 in order to move individual seeds out of seed holder 20 and into a needle for placement within tissue. When slot 55 contains two parallel rows of seeds, the portion of slot 55 through which channel 68 passes can be configured (e.g., sloped) such that seeds can funnel into channel 68 one at a time.

Seed holder 20 also can have external threads 70 and ridge 72, which can be positioned toward distal end 50. External threads 70 of seed holder 20 can interact with internal threads 44 of housing 15 when seed magazine 10 is assembled. Ridge 72 can be used as a stop so that a user knows when seed holder 20 is fully installed in housing 15 (e.g., a user can screw housing 15 onto seed holder 20 until ridge 72 abuts proximal end 38 of housing 15). External threads 70 of seed holder 20 and internal threads 44 of housing 15 can be configured such that a minimum number of rotations are necessary to fully and securely install housing 15 on seed holder 20. For example, the threads can be configured such that three, four, five, or more than five rotations are necessary to install housing 15 on seed holder 20 such that ridge 72 abuts proximal end 38 of housing 15. In this configuration, the force required to strip external threads 70 and internal threads 44 can be less than the force required to break seed magazine 10, thus reducing the risk of magazine breakage by over-tightening of housing 15 on seed holder 20.

With further reference to FIG. 5, bottom surface 60 and proximal end 52 of seed holder 20 can define recess 75. Brachytherapy devices such as the Mick® 200-TP and 200-TPV seed applicators typically contain a magazine retaining structure such as a ball-plunger, for example. Such structures can become jammed or otherwise unworkable after repeated use and sterilization. Recess 75 can be configured such that seed holder 20 will not interact (or will interact minimally) with a magazine retaining structure, and any jamming of a magazine retaining structure will not affect the insertion or removal of seed holder 20 into/from a device. Recess 75 can have any length, width, and depth. For example, recess 75 can have a length between 0.5 millimeter and 8 millimeters (e.g., 0.75, 1, 1.5, 2, 2.5, 3, 3.5, 4, 4.3, 4.5, 4.8, 5, 5.3, 5.5, 5.8, 6, 6.5, 7, 7.5, or 7.75 millimeters). Recess 75 can have a maximum width between 0.1 millimeter and 3 millimeters (e.g., 0.15, 0.2, 0.3, 0.5, 0.75, 1, 1.5, 2, 2.5, or 2.75 millimeters). Recess 75 can have a depth between 0.1 millimeter and 3 millimeters (e.g., 0.15, 0.2, 0.3, 0.4, 0.5, 0.75, 1, 1.5, 2, 2.5, or 2.75 millimeters).

Recess 75 can define a channel that extends along bottom surface 60 to proximal end 52 of seed holder 20. The channel defined by recess 75 can have a solid bottom surface, such that recess 75 does not extend into a cavity (e.g., the slot where the seeds can be placed) of seed holder 20. A channel defined by recess 75 can have opposing walls. Typically, no more than two surfaces of seed holder 20 (e.g., bottom surface 60 and proximal end 52) define recess 75. Recess 75 can have a width that is narrower than the width of cut-out 77. Recess 75 also can be centrally located between two edges of at least one of the surfaces of seed holder 20, and typically is not located at a corner of seed holder 20 where three surfaces can come together to form a point. Recess 75 can be non-circular in shape.

Bottom surface 60, side surface 64, and proximal end 52 of seed holder 20 can define cut-out 77. Cut-out 77 can be configured to fit around a placement pin within a brachytherapy device such as a Mick® 200-TP or 200-TPV seed applicator. Thus, cut-out 77 can facilitate the proper insertion of seed magazine 10 into a brachytherapy device having a placement pin, as seed magazine 10 can be fully inserted into such a device only when cut-out 77 faces the placement pin. Cut-out 77 can have a width that is greater than that of recess 75. Typically, three surfaces of seed holder 20 (e.g., bottom surface 60, side surface 64, and proximal end 52) define cut-out 77. Cut-out 77 can be configured such that a channel is not formed. For example, cut-out 77 can be configured such that it lacks two opposing walls.

Seed holder 20 can have a retention member such as spring 78, which can be defined by top surface 57 as shown in FIG. 5. Alternatively, bottom surface 60, first side surface 62, or second side surface 64 can define such a retention spring. When top surface 57 defines spring 78, first side surface 62 can define space 80 such that spring 78 can flex at least partially into space 80 when seed holder 20 is inserted into a brachytherapy device. If bottom surface 60, first side surface 62, or second side surface 64 define a retention spring, an adjacent surface can define a space analogous to space 80. Space 80 can have any length, width, and depth. For example, space 80 can have a length between 0.5 millimeter and 6 millimeters (e.g., 0.75, 1, 1.5, 2, 2.5, 3, 3.5, 4, 4.5, 5, 5.5, or 5.75 millimeters), a width between 0.1 millimeter and 3 millimeters (e.g., 0.15, 0.2, 0.3, 0.4, 0.5, 0.75, 1, 1.5, 2, 2.5, or 2.75 millimeters), and a depth between 0.1 millimeter and 3 millimeters (e.g., 0.15, 0.2, 0.3, 0.4, 0.5, 0.75, 1, 1.5, 2, 2.5, or 2.75 millimeters). Space 80 can define a bottom surface, such that it does not extend into a cavity (e.g., the slot where the seeds can be placed) of seed holder 20. Space 80 typically is not located at a corner of seed holder 20 where three surfaces can come together to form a point. Space 80 can have a width that is narrower than that of cut-out 77.

Figure 7:
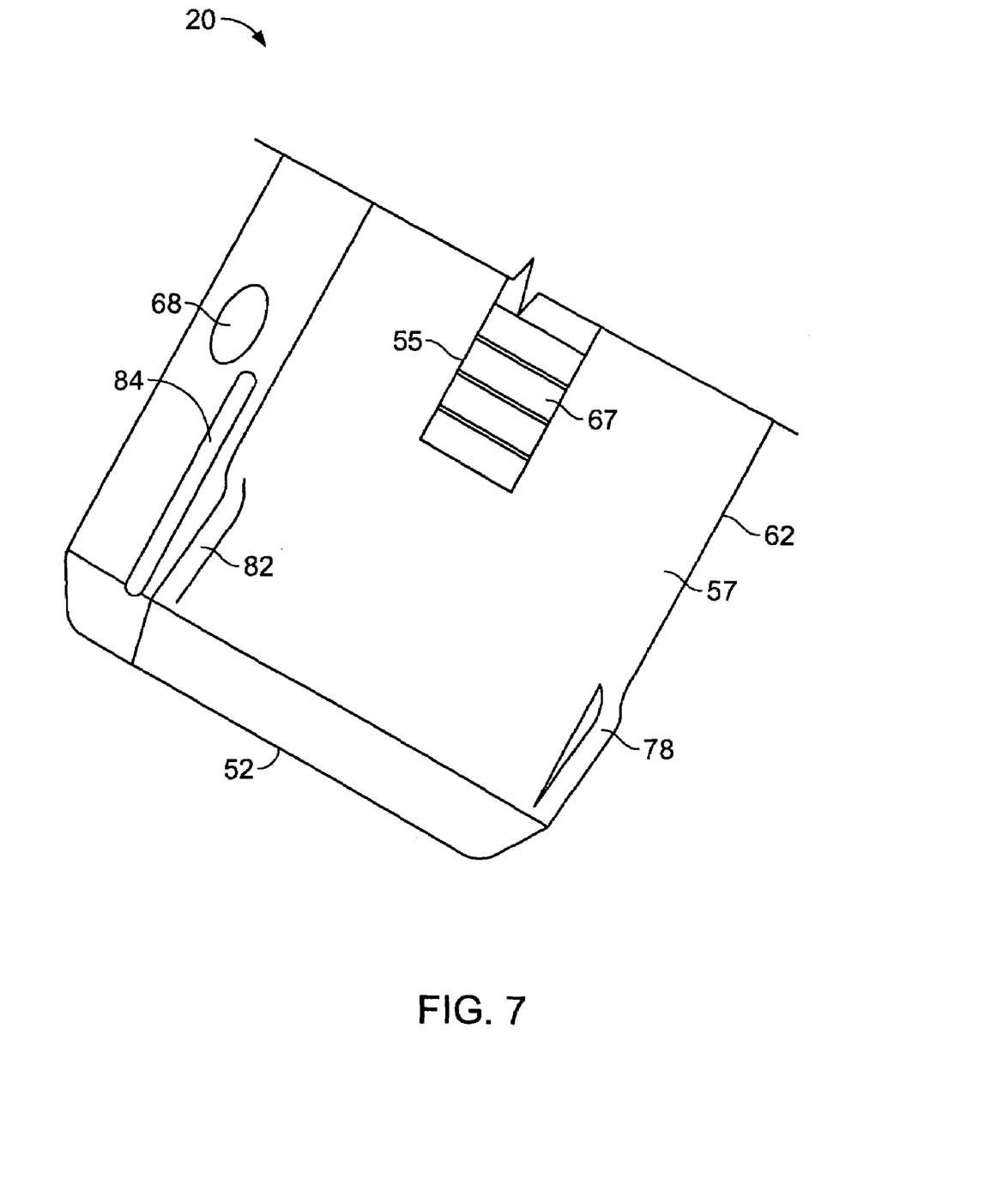
FIG. 7 is a close-up view of the proximal end of the seed holder of a seed magazine.

FIG. 7 is a close-up view of proximal end 52 of seed holder 20, showing spring 78. With reference to FIG. 7, top surface 57 of seed holder 20 also can define spring 82, while second side surface 64 can define space 84 under spring 82 so that spring 82 can flex when seed holder 20 is inserted into a brachytherapy device. FIG. 7 also shows seeds (e.g., seed 67) in slot 55 of seed holder 20.

Figure 8:
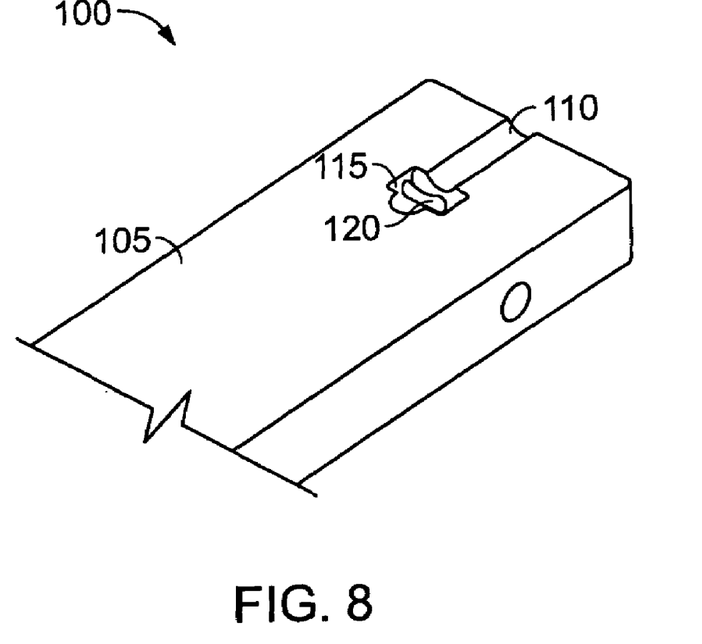
FIG. 8 is a view of the proximal end of the seed holder of a seed magazine, showing an alternative retention member.
Figure 9:
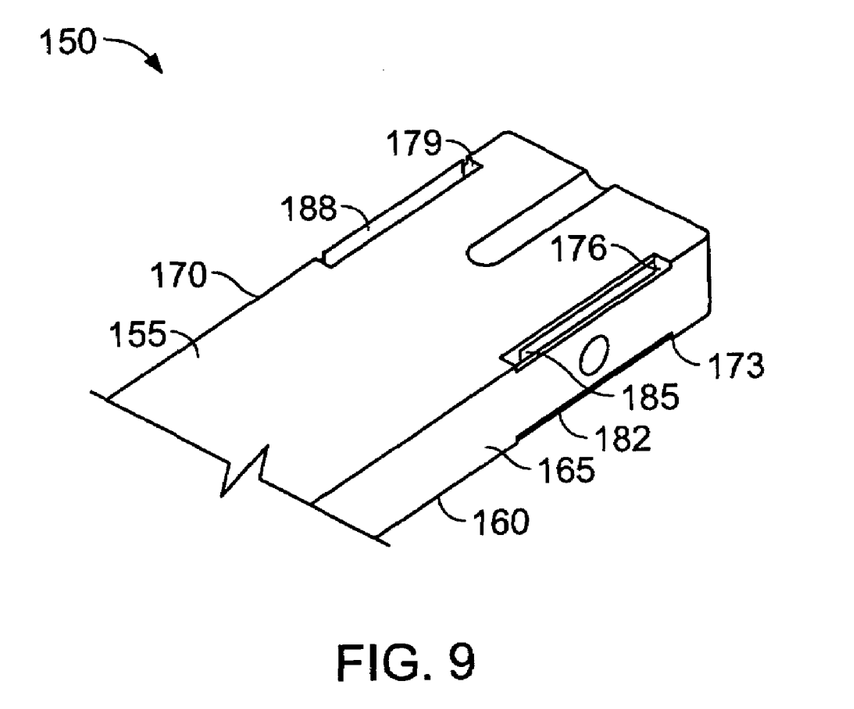
FIG. 9 is a view of the proximal end of the seed holder of a seed magazine, showing an alternative retention member.
Figure 10:
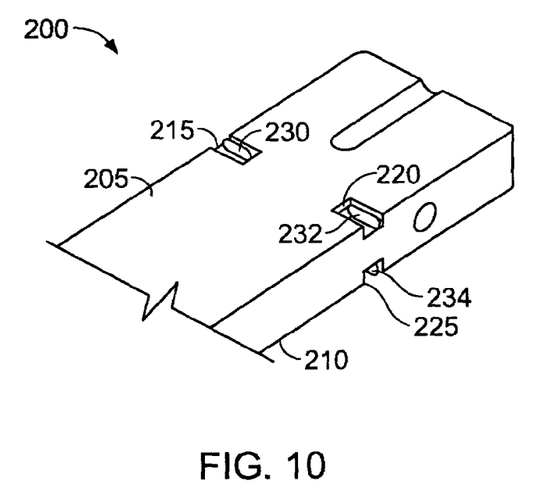
FIG. 10 is a view of the proximal end of the seed holder of a seed magazine, showing an alternative retention member.

FIGS. 8, 9, and 10 depict seed holders having other embodiments of a retention member. As depicted in FIG. 8, seed holder 100 can have top surface 105, which can define recess 110. Recess 110 further can define space 115, which can contain protrusion 120. Protrusion 120 can extend from seed holder 100 and, when seed holder 100 is inserted into a brachytherapy device, can exert force against the brachytherapy device such that seed holder 100 is retained within the device. For example, protrusion 120 can exert force on a magazine retaining structure (e.g., the ball of a jammed ball-plunger) within a brachytherapy device such that seed holder 100 is retained within the device. Protrusion 120 also can be flexible such that it snaps into place below a magazine retaining structure (e.g., the ball of a jammed ball-plunger) within a brachytherapy device and thus retains seed holder 100 within the device.

With reference to FIG. 9, seed holder 150 can have top surface 155, bottom surface 160, first side surface 165, and second side surface 170. The junctions of these surfaces can define one or more (e.g., one, two, three, four, or more than four) notches, such as notches 173, 176, and 179, and a fourth notch at the junction of bottom surface 160 and second side surface 170 (not visible in FIG. 9). Notches 173, 176, and 179 can be defined by two surfaces of seed holder 150 (e.g., bottom surface 160 and second side surface 170). Alternatively, notches 173, 176, and 179 can extend to an end of seed holder 150 and thus can be defined by three surfaces. Notches 173, 176, and 179 can have widths that are narrower than the width of cut-out 77. Notches 173, 176, and 179 can contain protrusions 182, 185, and 188, respectively. These protrusions can extend from seed holder 150 and, when seed holder 150 is inserted into a brachytherapy device, can exert force against the brachytherapy device such that seed holder 150 is retained within the device.

As shown in FIG. 10, seed holder 200 can have top surface 205 and bottom surface 210, which can define one or more (e.g., one, two, three, four, or more than four) notches, such as notches 215, 220, and 225, and a fourth notch on bottom surface 210 (not visible in FIG. 10). Notches 215, 220, and 225 can be narrower than cut-out 77. Notches 215, 220, and 225 typically are defined by two surfaces of seed holder 200, are not located where three surfaces can come together to form a point. Notches 215, 220, and 225 can form channels in seed holder 200, and typically do not extend into a cavity (e.g., a slot where seeds can be placed) of seed holder 200. Notches 215, 220, and 225 can contain protrusions 230, 232, and 234, respectively. These protrusions can extend from seed holder 200 and, when seed holder 200 is inserted into a brachytherapy device, can exert force against the brachytherapy device such that seed holder 200 is retained within the device.

Figure 11:
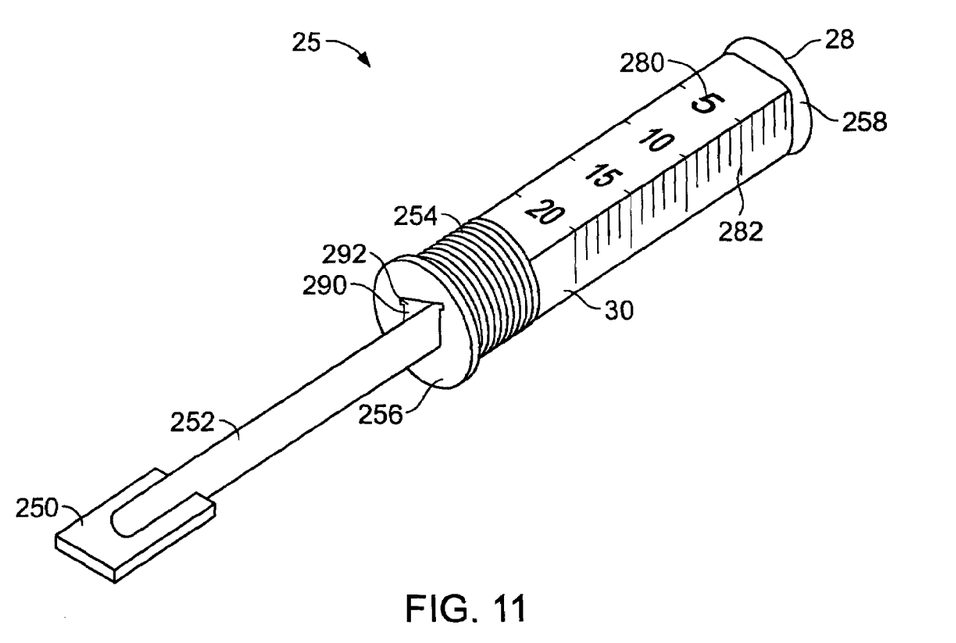
FIG. 11 is a side view of the pusher of a seed magazine.

FIG. 11 is a close-up view of pusher 25. With reference to FIGS. 3 and 11, pusher can have paddle 250 and stem 252 in addition to distal end 28 and gauge member 30. Paddle 250 can be configured to fit into slot 55 of seed holder 20, and can exert force on seeds that are contained within seed holder 20 when seed magazine 10 is assembled, for example. Stem 252 also can be configured to fit into slot 55, such that when no seeds are present in seed holder 20, paddle 250 can contact the end of slot 55 that is nearest proximal end 52 of seed holder 20. Pusher 25 also can have spring 254 (shown compressed in FIGS. 3 and 11) and plate 256. When pusher 25 is in an assembled seed magazine, spring 254 can extend between plate 256 and the distal end of the housing interior, and can cause pusher 25 to exert force against any seeds in slot 55. Spring 254 can be made from any suitable material, including a metal such as stainless steel or brass, for example. Spring 254 can be designed as a standard helical spring and can work close to its yield strength at full compression. Thus, spring 254 can provide a near constant force on seeds within slot 55, regardless of how many seeds are present within slot 55.

Figure 12:
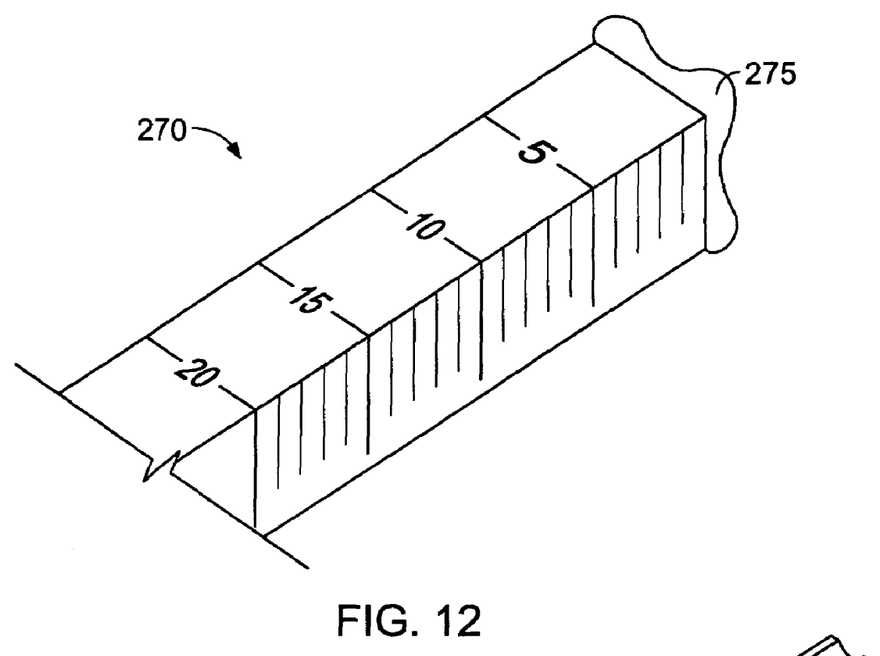
FIG. 12 is a close-up view of the distal end of the pusher of a seed magazine.

Distal end 28 of pusher 25 can define disc 258, which can be flexible enough to be pushed through the distal opening of a seed magazine housing but then can return to its original shape once distal end 28 extends through the opening. The diameter of disc 258 can be slightly larger than the distal opening of the housing, such that disc 258 can retain pusher 25 in the housing once distal end 28 has been pushed through the opening. Disc 258 can define any shape. As shown in FIG. 11, for example, disc 258 is circular. FIG. 12 shows pusher 270 with disc 275, which has a cloverleaf shape with four "petals." Alternatively, disc 258 can have any other shape (e.g., a square or triangular shape, a sunburst shape having multiple points extending from a circular center, or a circular shape with scalloped edges or "petals"). The geometry of disc 258 can be configured to provide different insertions and removal forces (e.g., such that less force is required to insert disc 258 through the distal opening of a seed magazine housing than to remove disc 258 from the housing). For example, the thickness of disc 258 can vary such that the edge of disc 258 has a thickness that is less than the thickness at a point away from the edge and closer to the center of disc 258. Alternatively, disc 258 can be of uniform thickness and have different insertion and removal forces. For example, disc 258 can be concave or dome-shaped, such that less force is required to insert disc 258 through the distal opening of a seed magazine housing than to remove disc 258 from the housing.

With further reference to FIG. 11, gauge member 30 of pusher 25 can have markings such as numerical marking 280 and/or gauge marking 282. When pusher 25 is assembled into a seed magazine containing seeds, such that gauge member 30 and distal end 28 protrude from the housing, a user can ascertain how many seeds are present in the magazine by reading the marking that is closest to the distal end of the housing. For example, if five seeds are present in a seed magazine, only the portion of gauge member 30 from distal end 28 to marking 282 will protrude from the housing, indicating that the magazine contains "5" seeds. Numerical markings and gauge markings can be imprinted on, molded into, or etched into gauge member 30 in any manner.

Gauge member 30 can have any shape. As shown in FIG. 11, for example, a cross section of gauge member 30 defines a square. Alternatively, a gauge member 30 can be configured such that a cross section defines a circle, a rectangle, an oval, a triangle, or any other shape. When gauge member 30 has four sides as in FIG. 11, adjacent sides can have numerical and gauge markings. Thus, opposite faces of gauge member 30 can have numerical markings, while the other two opposite faces can have gauge markings.

Figure 13:
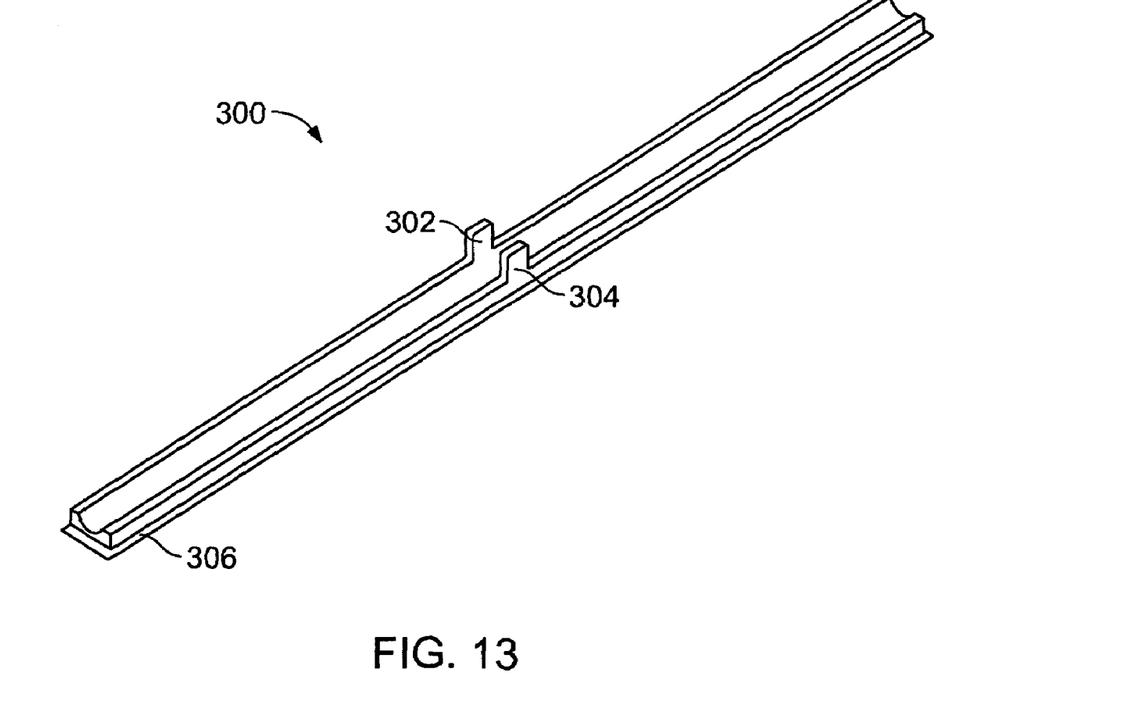
FIG. 13 is a side view of a shield for a seed magazine.

Gauge member 30 can be hollow and thus can define interior space 290. Interior space 290 can include groove 292 and can be configured to house a shield such as shield 300, shown in FIG. 13. When a seed magazine is assembled, shield 300 can extend from interior space 290 through the interior of the housing and over the slot of the seed holder, thus shielding a user from radioactive seeds contained within the magazine. Shield 300 and interior space 290 can be configured such that shield 300 can slide within interior space 290. Thus, when a user holds the seed magazine in what is typically considered an upright position (i.e., with the seed holder at the bottom), shield 300 can slide downward out of interior space 290 to cover any seeds in the seed holder. A user can turn the seed magazine over from the upright position (i.e., such that the seed holder is at the top) in order to allow shield 300 to slide back into interior space 290, thus enabling the user to visualize any seeds in the slot of the seed holder. Shield 300 can have protrusions 302 and 304, which can prevent shield 300 from sliding completely out of a seed magazine. For example, when a seed magazine is in an upright position such that the seed holder is at the bottom, shield 300 can slide down until protrusions 302 and 304 abut the distal end of the seed holder, thus preventing shield 300 from sliding any further. When a seed magazine is inverted such that the seed holder is at the bottom, shield 300 can slide toward the distal end of the pusher until protrusions 302 and 304 abut a plate (e.g., plate 256) on the pusher.

Figure 14:
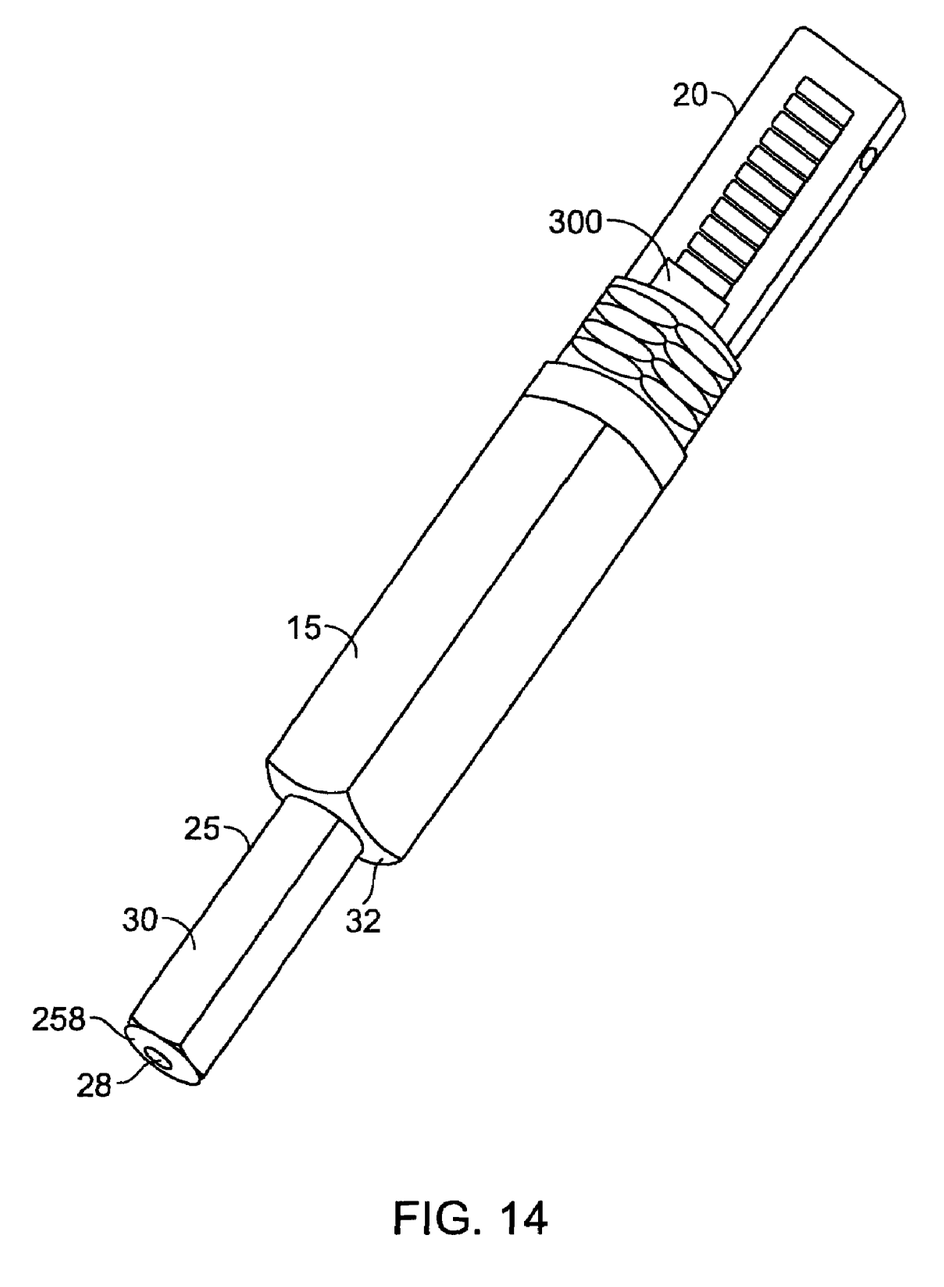
FIG. 14 is a side view of an assembled seed magazine having a shield.

Shield 300 also can have guide structure 306, which can be configured to fit into groove 292 of interior space 290. This embodiment can facilitate the smooth sliding movement of shield 300. FIG. 14 shows seed magazine 10 fully assembled, having housing 15, seed holder 20, pusher 25, and shield 300 partially extending over seeds in seed holder 20.

With reference to FIGS. 3, 4, 5, and 11, seed magazine 10 can be assembled by inserting shield 300 into interior space 290 of pusher 25. Pusher 25 with spring 254 in place can be inserted into housing 15 such that disc 257 extends through distal opening 35. Paddle 250 of pusher 25 then can be inserted into slot 55 of seed holder 20. Seed holder 20 and housing 15 can be pushed toward one another until distal end 50 of seed holder 20 abuts proximal end 38 of housing 15, at which point internal threads 44 of housing 15 can be screwed onto external threads 70 of seed holder 20. If seeds are present in slot 55, stem 252 can be pushed into housing 15, gauge member 30 can extend from distal end 32 of housing 15, and spring 254 of pusher 25 can be compacted against the interior distal end of housing 15, thus causing pusher 25 to exert force against the seeds. If no seeds are present within slot 55, spring 254 can cause paddle 250 to extend fully into slot 55, and gauge member 30 typically will not extend through distal opening 35 of housing 15.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A seed magazine comprising a housing, a seed holder, and a pusher, wherein said seed holder comprises a surface defining a channel having two opposing walls and being at least one millimeter in length, wherein said channel extends to an end of said seed holder and wherein said channel is centrally located between two edges of said surface.

2. The seed magazine of claim 1, wherein said seed holder comprises a proximal end and a distal end, and wherein said channel extends from said proximal end toward said distal end.

3. The seed magazine of claim 1, wherein no more than two surfaces of said seed holder define said channel.

4. The seed magazine of claim 1, wherein said channel is between three and eight millimeters in length.

5. The seed magazine of claim 1, wherein said channel is between five and six millimeters in length.

6. The seed magazine of claim 1, wherein the maximum width of said channel is less than five millimeters.

7. The seed magazine of claim 1, wherein the maximum width of said channel is between 0.5 and 2.5 millimeters.

8. The seed magazine of claim 1, wherein said seed holder comprises two adjacent surfaces, wherein the first of said surfaces defines at least one spring and the second of said surfaces defines a space, and wherein said space is positioned such that said at least one spring can move at least partially into said space when force is applied to said first surface.

9. The seed magazine of claim 1, wherein said seed holder comprises a surface, wherein said surface defines a protrusion, and wherein said protrusion exerts force against a brachytherapy device when said seed magazine is engaged with said brachytherapy device.

10. The seed magazine of claim 1, wherein said seed magazine further comprises a shield, wherein said seed holder defines a slot for retaining radioactive seeds, and wherein at least a portion of said shield is positioned over said seed holder.

11. The seed magazine of claim 10, wherein said shield is slidably movable within said housing and said pusher.

12. The seed magazine of claim 10, wherein said shield slidably moves within said housing and said pusher to obstruct the view of radioactive seeds within said seed magazine.

13. The seed magazine of claim 1, wherein said pusher comprises markings.

14. The seed magazine of claim 13, wherein the space between said markings is equal to the thickness of a seed.

15. The seed magazine of claim 1, wherein said housing is hollow, wherein the external surface of said housing defines external threads, wherein the internal surface of said housing defines internal threads, and wherein said external and internal threads have the same pitch.

16. The seed magazine of claim 15, wherein said external and internal threads are offset to maximize the thickness of said housing between said external and internal threads.

17. The seed magazine of claim 1, wherein said pusher comprises a distal end and a disc at said distal end.

18. The seed magazine of claim 17, wherein said disc defines a circular shape with scalloped edges.

19. The seed magazine of claim 17, wherein said disc is flexible.

20. The seed magazine of claim 17, wherein the thickness at the edge of said disc is less than the thickness at a point away from said edge and toward the center of said disc.

21. The seed magazine of claim 17, wherein the thickness of said disc is uniform.

22. The seed magazine of claim 21, wherein said disc is dome-shaped.

23. A seed magazine comprising a housing, a seed holder, and a pusher, wherein said seed holder comprises a surface defining a recess at least one millimeter in length and a cutout adjacent an edge of the surface and adjacent the recess, the recess extends to an end of said seed holder and is continually located between two edges of said surface.

* * * * *